United States Patent [19]

Nakano et al.

[11] Patent Number: 4,935,415

[45] Date of Patent: Jun. 19, 1990

[54] UCN-01 AND PROCESS FOR PRODUCTION THEREOF

[75] Inventors: Hirofumi Nakano; Isami Takahashi, both of Machida, Japan; Tatsuya Tamaoki, Brooklin, Mass.; Fusao Tomita, Machida, Japan; Isao Kawamoto, Hiratsuka, Japan; Kozo Asano, Machida, Japan; Makoto Morimoto; Hisayo Nomoto, both of Nagaizumi, Japan

[73] Assignee: Kyowa Hakko Kogyo Co., Ltd., Tokyo, Japan

[21] Appl. No.: 28,201

[22] Filed: Mar. 20, 1987

[30] Foreign Application Priority Data

Mar. 20, 1986 [JP] Japan .................................. 61-63704

[51] Int. Cl.$^5$ ..................... A61K 31/40; A61K 31/55; C07D 498/22
[52] U.S. Cl. .................................. 514/211; 435/128; 435/886; 514/908; 540/545
[58] Field of Search ................. 540/545; 514/211, 908

[56] References Cited

U.S. PATENT DOCUMENTS 4,524,145  6/1985  Matson .............................. 514/403

FOREIGN PATENT DOCUMENTS 296110  12/1988  European Pat. Off. ............ 540/545
2120388  6/1987  Japan ................................ 540/545
2240689  10/1987  Japan ................................ 540/545

OTHER PUBLICATIONS

Goff, Journal of the Chemical Society Chemical Communications (1978), p. 777.
Takahashi et al., Chem. Abst. 108-87679y (1988).
Nomoto et al., Chem. Abst 108-93097y (1988).

*Primary Examiner*—Cecilia Shen
*Attorney, Agent, or Firm*—Antonelli, Terry & Wands

[57] ABSTRACT

UCN-01 having an anti-tumor activity and an anti-bacterial activity is produced by culturing a microorganism belonging to the genus Streptomyces.

2 Claims, 2 Drawing Sheets

UCN-01 AND PROCESS FOR PRODUCTION THEREOF

BACKGROUND OF THE INVENTION

The present invention relates to UCN-01 and a process for production thereof. UCN-01 has an anti-tumor activity and an anti-bacterial activity and is useful as an anti-tumor agent, a bactericide, etc.

The present inventors have made screening of microorganisms producing a substance with a useful pharmacological activity and have found that a microorganism belonging to the genus Streptomyces isolated from the soil in Tsuno-gun, Yamaguchi Prefecture, produces a substance having an anti-tumor activity and an anti-bacterial activity. As a result of further investigations, the present inventors have successfully isolated and purified an active substance UCN-01 and have confirmed from its physicochemical properties that UCN-01 is a novel substance, and thus the present invention has been established.

Staurosporine, which is structurally analogous to UCN-01, is described in J. C.S. Chem. Comm., pp.800–801 (1978). UCN-01 has a superior anti-tumor activity as compared with staurosporine.

SUMMARY OF THE INVENTION

The novel substance UCN-01 having an anti-tumor activity and an anti-bacterial activity is specified by the following physicochemical properties:

(a) Molecular formula: $C_{28}H_{26}N_4O_4$ (b) Melting point: 245°–250° C. (decomposed)

(c) UV absorption spectrum: shown in FIG. 1 (measured in MeOH)

(d) IR absorption spectrum: shown in FIG. 2 measured by the KBr method (e) Optical rotation: $[\alpha]_D^{22} + 132.0°$ (c=0.3, MeOH)

(f) Solubility:

Soluble in methanol, chloroform, and dimethylsulfoxide, but scarcely soluble in water and hexane (g) $^1$H-NMR spectrum (measured in $CDCl_3$, internal standard TMS)

δ(ppm): 9.3(1H, d), 8.5(1H, d), 7.9(1H, d), 7.5–7.2(6H, m), 6.6(1H, s), 6.5(2H, d), 3.9(1H, d), 3.4(3H, s), 3.3(1H, d), 2.7–2.6(1H, m), 2.4(1H, m), 2.3(3H, s), 2.0–1.7(1H, br), 1.6(3H, s)

(h) $^{13}$C-NMR spectrum (measured in $CDCl_3$, internal standard TMS)

δ(ppm): 171.5, 140.2, 137.2, 132.9, 131.2, 128.1, 126.5, 125.5, 124.8, 123.8, 123.2, 123.0, 120.2, 120.1, 117.5, 115.2, 115.1, 115.0, 107.1, 91.2, 84.1, 80.2, 79.5, 57.4, 50.6, 33.4, 30.2, 29.7

From the foregoing physicochemical properties, the structural formula of UCN-01 is determined to be as follows:

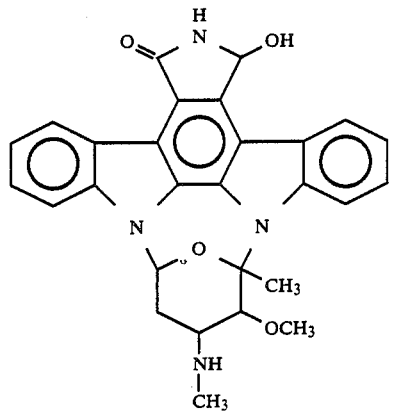

UCN-01 can be prepared by culturing a UCN-01-producing strain belonging to the genus Streptomyces.

DETAILED DESCRIPTION OF THE INVENTION

Figure 1:
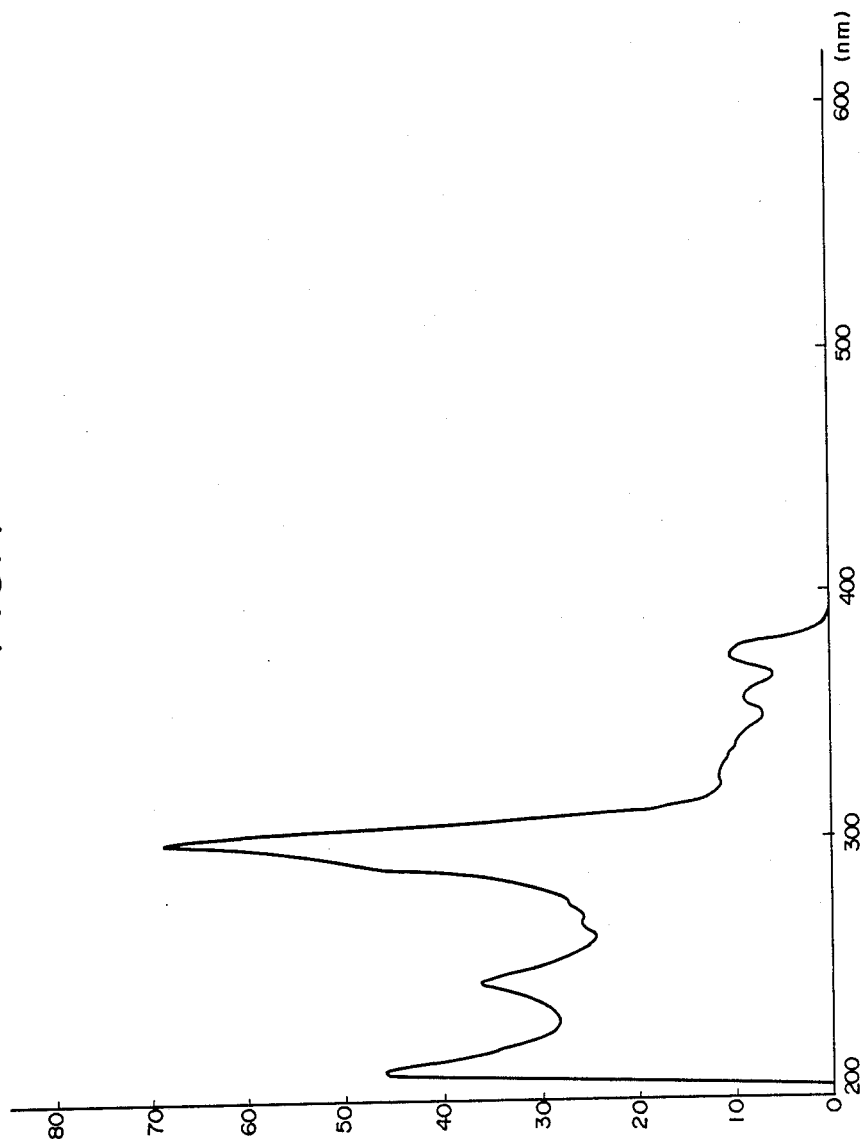
FIG. 1 shows UV absorption spectrum of UCN-01.
Figure 2:
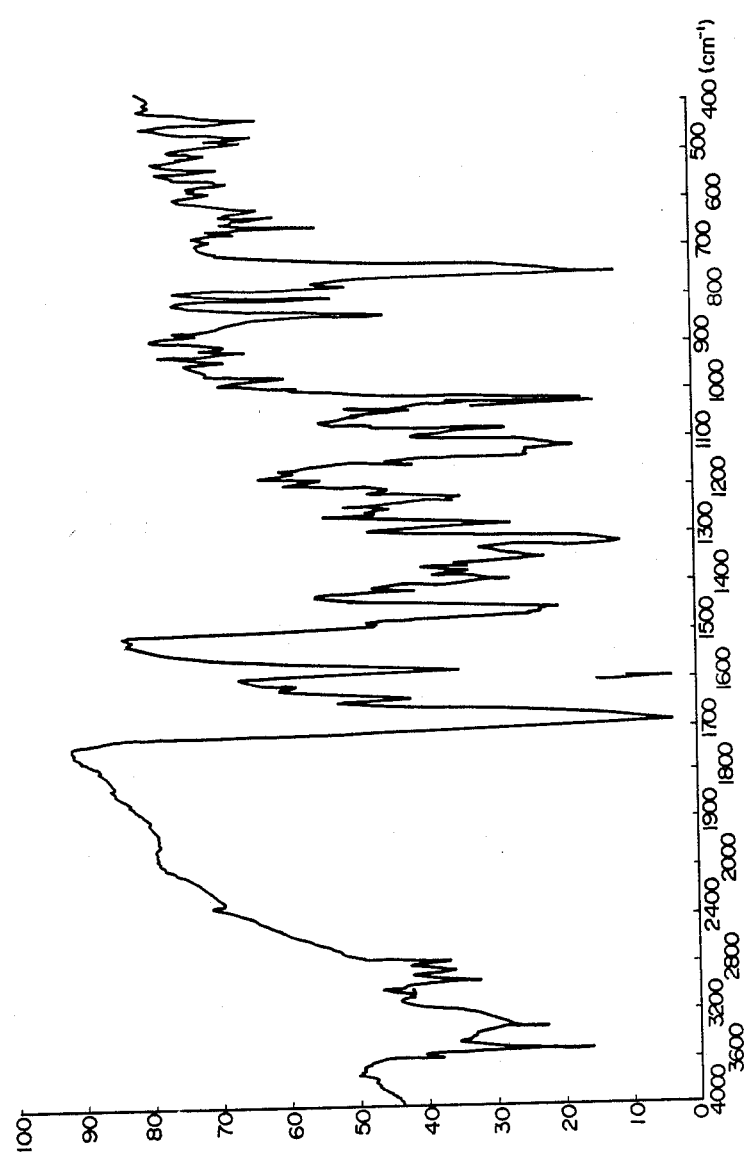
FIG. 2 shows IR absorption spectrum of UCN-01.

UCN-01 can be obtained by culturing a UCN-01-producing strain belonging to the genus Streptomyces in a medium, and recovering UCN-01 from the culture liquor. Any microorganism can be used in the process of the present invention, so long as it is a strain belonging to the genus Streptomyces and having an ability to produce UCN-01.

As the typical strain to be used, UCN-01 strain isolated from the soil in Tsuno-gun, Yamaguchi Prefecture can be mentioned.

Morphological characteristics, physiological properties and growth conditions in various agar media of UCN-01 strain are shown in Tables 1 to 3, respectively.

TABLE 1

| Morphology | |
|---|---|
| Aerial mycelium: | It is branched but not fragmented. |
| Substrate mycelium: | It is branched but not fragmented. |
| Spore: Chains of more than 20 spores are formed at the end of simply branched aerial mycelium; it is spiral to open spiral. | |
| Shape and size of spore: Smooth, oval to cylindrical, 0.5 to 0.7 × 0.7 to 1.0 μm | |
| Motility of spore: Negative | |
| Color | |
| Aerial mycelium: | Extremely pale purplish grey or white |
| Substrate mycelium: | Colorless or beige, brown or chocolate color. |
| Soluble pigment: | Yellow to brownish orange |
| Chemical Composition | |
| Cell wall amino acid: LL-diaminopimelic acid, glycine, alanine, glutamic acid. | |

TABLE 2

| (1) Assimilation of carbon sources | |
|---|---|
| Carbon Source | Growth |
| D-Glucose | ++ |
| L-Arabinose | − |

TABLE 2-continued

|  |  |
|---|---|
| D-Xylose | − |
| Inositol | − |
| D-Mannitol | − |
| D-Fructose | − |
| L-Rhamnose | − |
| Sucrose | − |
| Raffinose | − |
| Melibiose | − |
| Erythritol | − |
| Mannose | − |
| D-Ribose | + |
| Adonitol | − |
| Glycerol | + |
| Lactose | − |
| Methylglucoside | − |
| D-Galactose | − |
| Starch | + |

(2) Liquefaction of gelatin: Positive
(3) Hydrolysis of starch: Positive
(4) Coagulation and peptonization of defatted milk: Both positive
(5) Formation of melanin-like pigment: Positive
(6) Growth temperature range (optimum): 20 to 32° C. (28 to 30° C.)
(7) Salt resistance: Grow at NaCl concentration up to 3%

Note (1) −: no growth +: moderate growth ++: good growth
Note (2) Growth temperature range indicates the results obtained by observation for 2 days. The action on defatted milk and cellulose indicates the results obtained by observation for 1 month. With respect to the other items, the results obtained by observation for 2 weeks at 28° C. are shown.

TABLE 3

| Medium | Growth Condition |
|---|---|
| Sucrose-nitrate agar medium | G: extremely poor<br>AM: scant, cloud pink (7 cb)<br>SM: colorless<br>P: negative |
| Glucose-asparagine agar medium | G: good<br>AM: abundant, white (a) to light mustard tan (2 ie) to down blue (15 dc)<br>SM: light wheat (2 ea)<br>P: negative |
| Glycerine-asparagine agar medium | G: moderate<br>AM: fair, white (a)<br>SM: light amber (3 ic)<br>P: pale honey gold |
| Starch agar medium | G: good<br>AM: abundant, orchid haze (10 dc)<br>SM: light tan (3 gc)<br>P: negative |
| Tyrosine agar medium | G: moderate<br>AM: scant to fair, orchid haze (10 dc)<br>SM: chocolate (5 nl)<br>P: pale chocolate |
| Nutrient agar medium | G: moderate<br>AM: abundant, pearl (3 ba) to dark covert gray (2 ih)<br>SM: gold (21 c)<br>P: extremely pale yellow |
| Yeast extract-malt extract agar medium | G: moderate<br>AM: abundant, orchid mist (10 cb) to dusk (10 fe)<br>SM: bamboo (2 gc) to yellow maple (3 ng)<br>P: extremely pale yellow |
| Oatmeal agar medium | G: moderate<br>AM: fair, orchid tint (10 ba)<br>SM: colorless<br>P: golden brown (3 pi) |
| Peptone-yeast extract-iron agar medium | G: moderate<br>AM: scant, white (a)<br>SM: colorless<br>P: adobe brown (31 g) |
| Hickey-Tresner agar medium | G: good<br>AM: abundant, white (a) to orchid mist (10 cb)<br>SM: chestnut brown (4 ni)<br>P: negative |

Note (1) Culture: 28° C., 21 days
Note (2) Color indication: Color Harmony Manual. Container Corporation of America
Note (3) G: growth AM: formation of aerial mycelium and its color SM: color of substrate mycelium P: soluble pigment In addition to alanine and glutamic acid, LL-diaminopimelic acid and glycine were detected as cell wall amino acids, and the composition of cell wall was identified to be I type in chemical classification of Actinomycetales. Morphologically, it formed aerial mycelium simply branched and formed long spore chains at the end. Therefore, this strain was classified to the genus Streptomyces in Actinomycetales.

A strain having bacteriological properties akin to those of UCN-01 strain was searched for in the approved bacterial species, but no approved bacterial species identified to be the same as UCN-01 strain was found.

UCN-01 strain was named Streptomyces sp. UCN-01 and has been deposited with the Fermentation Research Institute, Agency of Industrial Science and Technology under FERM BP-990 on Feb. 20, 1986.

As the medium for culturing in the present invention, either a natural medium or a synthetic medium can be used so long as it appropriately contains carbon sources, nitrogen sources, inorganic materials, etc.

As the carbon source, glucose, starch, glycerol, mannose, fructose, sucrose, molasses, alcohols such as methanol and ethanol, organic acids such as acetic acid, formic acid, citric acid and malic acid, etc. can be used.

As the nitrogen source, ammonium chloride, ammonium sulfate, ammonium nitrate, sodium nitrate, urea, peptone, meat extract, yeast extract, dry yeast, corn steep liquor, soybean powder, Casamino acid, etc. can be used.

As the inorganic materials, sodium chloride, potassium chloride, ferrous sulfate, manganese sulfate, copper sulfate, potassium dihydrogen phosphate, dipotassium hydrogen phosphate, magnesium phosphate, magnesium sulfate, calcium carbonate, etc. can be used.

In addition, substances for accelerating production of UCN-01, for example, biotin, vitamins, etc. can also be supplemented to the medium.

Culturing is usually carried out by liquid culture, and most preferably by submerged stirring culture. Culturing temperature is 25° to 32° C., preferably 28° to 30° C. It is desirable to maintain the pH of the medium at 4 to 10, preferably 6 to 8 by adding aqueous ammonia or aqueous ammonium carbonate during the culturing. Usually, by liquid culture for 1 to 7 days, the desired product is produced and accumulated in the culture liquor. When the amount of the product in the culture liquor reaches the maximum, culturing is discontinued.

The desired product is isolated and purified from the culture liquor after the microbial cells have been removed by filtration.

For the isolation and purification of UCN-01 from the culture liquor, the ordinary method for isolating a microbial metabolite from its culture liquor can be utilized. For example, the culture liquor is separated into the culture filtrate and the microbial cells. The microbial cells are extracted with a solvent such as chloroform, acetone, etc., and the extract is concentrated under reduced pressure to remove the solvent therefrom. The residue is dissolved in water. The cell-free culture filtrate and the aqueous solution are passed through a column packed with a non-ionic porous resin, for example, HP-20 (manufactured by Mitsubishi Chemical Industries Ltd.) to adsorb the active component. Then, the adsorbed active component is eluted with methanol, acetone, etc. The eluate is concentrated to dryness, and water of pH 9 to 10 and ethyl acetate are added to the residue, followed by shaking, whereby the active component is shifted to the ethyl acetate layer. The lower aqueous layer is removed and then water of pH 2.5 is added thereto, followed by shaking, whereby the active component is shifted to the aqueous layer. Such a shift and dissolution operation is repeated several times and the active component is finally shifted to the ethyl acetate layer. The active component is dried to give a crude product. The thus obtained crude UCN-01 powder can be further purified by procedures such as recrystallization and various kinds of chromatography using Sephadex, silica gel, etc.

The biological properties of UCN-01 are shown below.

(A) Anti-bacterial activity

The minimum inhibitory concentration (MIC) against various microorganisms is shown below.

TABLE 4

| Microorganism | MIC ($\mu$g/ml) |
|---|---|
| Staphylococcus aureus ATCC 6538P | 83 |
| Bacillus subtilis No. 10707 | >100 |
| Klebsiella pneumoniae ATCC 10031 | 83 |
| Escherichia coli ATCC 26 | 83 |
| Shigella sonnei ATCC 9290 | 100 |
| Salmonella typhi ATCC 9992 | 83 |

The anti-bacterial activity was measured by the agar dilution method, using a medium (pH 7) prepared by dissolving 3 g of Bacto-Tryptone (manufactured by Difco Co., Ltd.), 3 g of meat extract, 1 g of yeast extract, 1 g of glucose and 16 g of agar in 1 l ( of water.

(B) Acute toxicity

The acute toxicity value ($LD_{50}$) was 30 mg/kg by intraperitoneal administration to mice.

(C) Anti-tumor activity

Therapeutic effect on lymphocytic leukemia P388 tumor:

Five male $CDF_1$ mice each having a weight of about 22 g were used for each group as test animals, and $1 \times 10^6$ cells of lymphocytic leukemia P388 tumor were implanted intraperitoneally in the test animals. 24 hours after implantation, 0.2 ml of a phosphate buffer saline (hereafter referred to as PBS) containing UCN-01 was intraperitoneally administered.

The composition of PBS was 0.8% NaCl, 0.02% KCl, 1.15% $Na_2HPO_4$, 5% $K_2HPO_4$ and 0.02% $KH_2PO_4$ (pH 7.0).

For comparison, 0.2 ml of PBS solution containing Staurosporine was intraperitoneally administered 24 hours after the implantation of the tumor cells. Increased life span (T/C) (T: mean survival days of the treated group, C: mean survival days of the control group) is shown in Table 5.

TABLE 5

| Compound | Dose (mg/kg) | Increased Life Span (T/C) |
|---|---|---|
| UCN-01 | 0 (control) | — |
| | 7.5 | 1.12 |
| | 15 | 1.24 |
| | 30 | toxic |
| Staurosporine | 1 | 1.10 |
| | 2 | 1.12 |
| | 4 | 1.08 |

Notes:
1 $LD_{50}$ of Staurosporine is 6.6 mg/kg.
2 Staurosporine is described in J. C.S. Chem. Comm., pp. 800-801 (1978) and its structural formula is shown below.

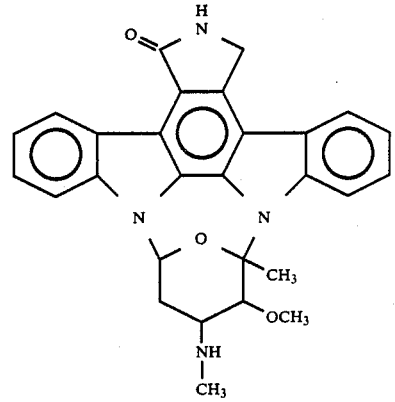

UCN-01 has an anti-tumor activity and an anti-bacterial activity and is useful as an anti-tumor agent, a bactericide, etc. The dose of UCN-01 to be administered to a human being is 0.01–20 mg/kg/day.

UCN-01 may be administered in the form of tablets, capsules, powder, granules, suppository, injection, etc. prepared in the ordinary manner, depending on the administration form.

For example, in the case of tablets, capsules, powder, granules and suppository, UCN-01 may be contained in an amount of 0.1–85% by weight. As other components (carriers), commonly employed excipients such as glucose, lactose, avicel, etc., disintegrators such as starch, calcium carboxymethylcellulose, etc., lubricants such as magnesium stearate, talc, etc., binders such as polyvinyl alcohol, gelatin, etc., and the like may be employed.

In the case of injection, UCN-01 may be contained in an amount of 0.05–50 mg /2–50 ml. An injection solution can be prepared using a carrier such as physiological saline, glucose solution, lactose solution or mannitol solution.

Certain specific embodiments of the present invention are illustrated by the following examples.

EXAMPLE 1

Streptomyces sp. UCN-01 strain was used as a seed strain. The strain was inoculated in 300 ml of a seed medium (pH 7.2, prior to sterilization) containing 10 g/l Bacto-Tryptone (manufactured by Difco Co., Ltd.), 5 g/l yeast extract, 5 g/l NaCl and 1 g/l glucose in a 2 l-Erlenmeyer flask and subjected to shaking culture (200 rpm) at 30° C. for 48 hours. The resulting seed culture was inoculated in 15 l of a fermentation medium having the following composition in a 30 l-jar fermenter, and cultured at 30° C. for 72 hours with aeration and stirring (rotation: 250 rpm, aeration: 15 l/min).

Composition of the fermentation medium:

20 g/l glucose, 15 g/l soybean powder, 4 g/l calcium carbonate (pH 7.0, adjusted with NaOH prior to sterilization)

The pH of the medium was adjusted to 6.5-7.5 with aqueous ammonia during the culturing.

The microbial cells were separated from the culture liquor by filtration to give 13 l of a filtrate. Then, 13 l of the filtrate was passed through a column filled with 2 l of nonionic porous resin HP-20 (trademark, manufactured by Mitsubishi Chemical Industries Ltd.) to adsorb the active component. After washing with water, the column was further washed with 50% methanol to remove impurities, followed by elution with methanol. The eluted fraction was concentrated and adjusted to pH 10, followed by extraction with ethyl acetate. The ethyl acetate layer was transferred to 0.1N HCl and then the pH was adjusted to 10, followed by extraction with ethyl acetate. The extract was concentrated and developed with chloroform-methanol using silica gel (Wakogel C-200, Wako Junyaku) to give an active component. Then, the active component was developed with chloroform-methanol using silica gel (Lichroprep Si60, Merck) to give 5 mg of UCN-01. This fraction was dissolved in a small quantity of methanol. The solution was subjected to density gradient elution using high pressure liquid chromatography (Wakogel LC ODS 30 K, Wako Junyaku) with 50% methanol and 100% methanol to give pure UCN-01. The thus obtained UCN-01 showed the physicochemical properties and biological properties described hereinbefore.

EXAMPLE 2 (INJECTION)

2.0 g of UCN-01 was dissolved in 20 l of ethanol, and the solution was filtered through a millipore filter (pore diameter of 0.22 μ) under pressure to effect sterilization. The resulting sterilized filtrate was charged in brown vials in 5.0 ml portions and freeze-dried in a conventional manner to give a freeze-dried product of 0.5 mg/vial.

EXAMPLE 3 (TABLET)

Tablets were prepared from 180 mg of UCN-01, 90 mg of lactose, 40 mg of corn starch, 4 mg of polyvinyl alcohol, 28 mg of avicel and 1 mg of magnesium stearate.

What is claimed is:
1. UCN-01 represented by the following formula:

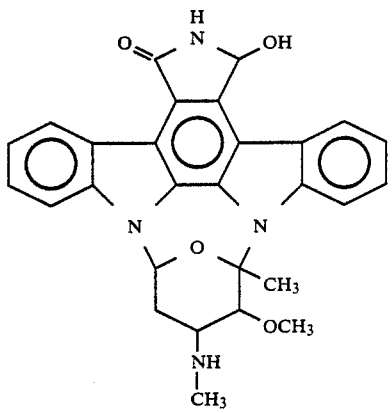

2. An antibacterial and/or anti-leukemia pharmaceutical composition comprising a pharmaceutical carrier and as an active ingredient, a therapeutically effective amount of UCN-01.

* * * * *